United States Patent [19]
Spindel et al.

[11] Patent Number: 5,814,463
[45] Date of Patent: Sep. 29, 1998

[54] SCREENING ASSAYS USING NUCLEIC ACIDS ENCODING RECEPTORS FOR BOMBESIN-LIKE PEPTIDES

[75] Inventors: Eliot R. Spindel, Lake Oswegor; Srinivasa Nagalla; Brenda Barry, both of Portland, all of Oreg.

[73] Assignee: The Medical Research Foundation of Oregon, Beaverton, Oreg.

[21] Appl. No.: 910,092

[22] Filed: Aug. 12, 1997

Related U.S. Application Data

[62] Division of Ser. No. 279,590, Jul. 22, 1994, Pat. No. 5,656,749.
[51] Int. Cl.$^6$ .......................... C12Q 1/00; C07K 14/705; C12N 15/12
[52] U.S. Cl. .......................... 435/7.2; 435/7.21; 435/69.1; 435/252.3; 435/254.11; 435/325; 530/350
[58] Field of Search .......................... 435/7.21, 69.1, 435/252.3, 254.11, 325, 7.2; 530/350

[56] References Cited

PUBLICATIONS

Battey and Wada, "Two distinct receptor subtypes for mammalian bombesin–like peptides," TINS, 14:524–528, 1991.
Battey et al., Molecular cloning of the bombes in/gastrin–releasing peptide receptor from Swiss T3T cells PNAS, 88:395–399 (1991).
Fathi, et al., "BRS–3: A Novel Bombesin Receptor Subtype Selectively Expressed in Testis and Lung Carcinoma Cells," The Journal of Biological Chemistry, 268:5979–5984, 1993.
Giladi, et al., "Molecular Cloning and Characterization of Receptors for the Mammalian Bombesin–Like Peptides," Journal of Molecular Neuroscience, 4:41–54, 1993.
Giladi and Spindel, "Simple Luminometric Assay to Detect Phosphoinositol–Linked Receptor Expression in Xenopus Oocytes," BioTechniques, 10:744–747, 1991.

Gorbulev, et al., "Molecular cloning of a new bombesin receptor subtype expressed in uterus during pregnacy," Eur. J. Biochem, 208:405–410, 1992.
Julius, et al., "Molecular Characterization of a Functional cDNA Encoding the Serotonin 1c Receptor," Science, 241:558–564, 1988.
Moody, T.W., et al., "Characterization of Receptors for Bombesin/Gastrin–Releasing Peptide in Human and Murine Cells," Methods Enzymol, 168:481–493, 1989.
Nagalla, et al., "Gastrin–releasing Peptide (GRP) Is Not Mammalian Bombesin," The Journal of Biological Chemistry, 267:6916–6922, 1992.
Spindel, et al., "Cloning and Functional Characterization of a Complementary DNA Encoding the Murine Fibroblast Bombesin . . . , " Molecular Endocrinology, 4:1956–1963, 1990.
Sandberg, et al., "Calcium mobilization by angiotensin II and neurotransmitter receptors expressed in *Xenopus Laevis* oocytes," FEBS Lett., 241:177–180, 1988.
Shirakawa, et al., "Interaction between stimuli and their antagonists on frog esophageal peptic glands" Am. J. Physiol. 249(6 pt 1):668–673 (1985).
Von Schrenck, et al., "Neuromedian B receptor in esophagus: evidence for subtypes of bombesin receptors," Bombesin Receptor Subtypes, 256:G–747–G758, 1989.
Wada, et al., "cDNA Cloning, Characterization, and Brain Region–Specific Expression of a Neuromedian–B–Preferring Bombesin Receptor," Neuron, 6:421–430, 1991.
Wada, et al., "Comparison of Gene Expression for Two Distinct Bombesin Receptor Subtypes in Postnatal Rat Central Nervous System," Molecular and Cellular Neurosciences, 3:446–460, 1992.

*Primary Examiner*—Sally P. Teng
*Attorney, Agent, or Firm*—William McGowan; John D. Conway; Fish & Richardson

[57] ABSTRACT

Pure nucleic acids encoding novel receptors for bombesin-like peptides, the novel receptors themselves, and their antibodies. Also disclosed is a method of screening for a compound capable of interacting with any of these novel receptors.

1 Claim, 4 Drawing Sheets

```
CACGAGTGCAAGCACTAAACCACCCTAGTGCTGATGAGAGCTGTGATTTCTGGAGATACCGAGTTTGTGGACATCAATTA
                    ^20                     ^40                     ^60                     ^80
GGTTTCATTTGTGGAACTTTAATTGAGGTCACTTGTGTGCTGCAATTCATGAACTTGAAACTGCTGAAGAAGAAATTGG
                    ^100                    ^120                    ^140                    ^160
                                                              MetProGluGlyPheGlnSerLeuAsnGlnThrLeuProSerAlaIleSer
                                                                                v10
AACAACTGAATTTATTAGATTAAAAAAAAAATGCCTGAAGGTTTCAGTCACTTAACCAGACATTGCCATCTGCTATAA
                    ^180                    ^200                    ^220                    ^240
                                   v20                                    v30                                    v40
SerIleAlaHisLeuGluSerLeuAsnAspSerPheIleLeuGlyAlaAlaLysGlnSerGluAspValSerProGlyLeu
GTAGCATAGCTCATTTGGAATCCCTAATTGACAGTTTCATTTTAGGTGCAAAGCAAAGTGAAGATGTATCCCCTGGGTTA
                    ^260                    ^280                    ^300                    ^320
                                                              v60                                    v70
GluIleLeuAlaLeuIleSerValThrTyrAlaValThrTyrAlaValIleLeuIleSerValGlyIleIleLeuIleLysVal
GAAATACTGGCTCTAATTCTGTCACATATGCTGTTATTATTCTGTCGGTATCCTTGGAAACACAATACTTATAAAAGT
                              ^340                    ^360                    ^380                    ^400
                                                                                v90
PhePheLysIleLysSerMetGlnThrValProAsnIlePheIleThrSerLeuAlaPheGlyAspLeuLeuLeuLeuLeu
ATTTTTAAAATCAAGTCAATGCAGACTGTTCCTAATATTTCATCACCAGCCTGGCTTTGGAGATCTTCTTCTACTGC
                    ^420                    ^440                    ^460                    ^480
                                                              v120
ThrCysValProValAspAlaSerArgTyrIleValAspThrTrpMetPheGlyArgAlaGlyCysLysIleIleSer
TGACCTGCGTGCCAGTGCCGACGCCATCCGGTATATTGTGGACACGTGGATGTTTGGAAGAGCTGGCTGTAAGATAATTTCC
                    ^500                    ^520                    ^540                    ^560
                                   v130                                    v140                                    v150
PheIleGlnLeuThrSerValGlyValValPheThrValLeuSerThrAspArgTyrArgAlaIleValAlaIleValLys
TTCATACAGTTACCTCTGTCGGAGTGTCGGTGTTTACTTAACTGTCCTCAGTACTGACACAGGTACAGAGCCATTGTGAA
                    ^580                    ^600                    ^620                    ^640

```
                                    v170
          ProLeuGlnThrSerAspAlaValLeuLysThrCysGlyLysAlaValCysValTrpIleIleSerMetLeuLeu
          ACCCTTGCAATTGCAGAGACCTCAGATGCCCGTTTTGAAGACATGTGGCAAAGCTGTTTGTGTTTGGATCATTCCATGCTCC
               ^660                    ^680                    ^700                    ^720
     v180                                                v200
   AlaAlaProGluAlaValPheSerAspLeuTyrGluPheGlySerSerGluLysAsnThrThrPheGluAlaCysAla
   TCGCTGCTCCAGAAGCTGTGTTCTCAGATTTGTATGAATTTGGCAGCTCGGAAAAAATACCACTTTGAAGCCTGTGCT
          ^740                    ^760                    ^780                    ^800
          v210                                            v230
        ProTyrProValSerGluLysIleLeuGlnGluThrHisSerLeuIleCysPheLeuValPheTyrIleValProLeuSer
        CCATATCCAGTCTCGAAAGATTCTGCAAGAGACACATTCCTAATATGCTTCCTGTATTCTACATTGTTCCCCTGTC
               ^820                    ^840                    ^860                    ^880
               v240                                         v250
      IleIleSerAlaTyrTyrPheLeuIleAlaLysThrLeuTyrLysThrPheAsnMetProAlaGluHisThrHis
      AATCATTCTGCATATTACTTCCTTATTGCAAAACCCTGTACAAAGTACTTTCAACATGCCCTGCTGAAGAGCACACTC
               ^900                    ^920                    ^940                    ^960
        v260                                            v280
      AlaArgLysGlnIleGluSerArgLysArgValAlaLysThrValLeuValAlaLeuPheAlaValCysTrp
      ACGGCCCGAAAACAGATAGAATCGCGCAAACGAGTGCAAAACTGTGCTGGTTCTGGTGGCGCTATTTGCTGTCTGTTGG
               ^980                    ^1000                   ^1020                   ^1040
        v290                                            v310
      LeuProAsnHisMetLeuTyrLeuTyrArgSerPheThrTyrHisSerAlaValAlaAsnSerSerAlaPheHisLeuSerAla
      CTCCCTAACCACATGCTCTACTTGTATCGATCCTTCACATATCACTCCGCAGTGAATTCCTCTGCGTTTCACCTGTCAGC
               ^1060                   ^1080                   ^1100                   ^1120
             v320                                            v330
      ThrIlePheAlaArgValLeuAlaLeuArgAsnSerCysValAsnProPheAlaLeuTyrTrpLeuSerArgSerPheArg
      CACAATCTTTGCGCGAGTACTGGCTTTGCGCAATTCCTGCCCTCAACCCCTTCGCCCTCTATTGGCTAAGCAGAGCTTTA
               ^1140                   ^1160                   ^1180                   ^1200
             v360                                         v360
      GlnHisPheLysLysGlnValTyrCysLysThrGluProThrLysSerAspProGlnGlnTyrHis
      GGCAGCATTTTAAAAGCAAGTGTATTGTTGTAAGACTGAACCTCTGCATCCAACAAAGTCCGACCCACAGCAGTACCAT
               ^1220                   ^1240                   ^1260                   ^1280
```

FIG. 1C

```
                          v370
AsnTrpAsnTyrArgCysGluArgGlnHisProAspVal (SEQ ID NO:2)
AACTGGAATTACCGCTGTGAAAGGCAACATCCAGATGTCTGAAATTAGCATTACATTAAGTGCTTACGATGTAAAGA
         ^1300             ^1320              ^1340             ^1360
AAGAGTGACAGTGTCGCCAAATAAGTTTATAAAACTTACTGTAAACAAAAGATGGATAAAGTTTTGTTG
         ^1380             ^1400              ^1420             ^1440
CTGCATATATTGACGTCTGTTTATTAAAAATCCAGAGTATAAAGTTTTATTACTACAAACAAAAAATATACCTCAACATTC
         ^1460             ^1480              ^1500             ^1520
TAACCACAATTGAATTATTCATATATTACCCTTATTTATTCAG (SEQ ID NO:1)
         ^1540             ^1560
```

… # SCREENING ASSAYS USING NUCLEIC ACIDS ENCODING RECEPTORS FOR BOMBESIN-LIKE PEPTIDES

This is a divisional of application Ser. No. 08/279,590, filed Jul. 22, 1994, now U.S. Pat. No. 5,656,749.

STATEMENT AS TO FEDERALLY SPONSORED RESEARCH

This invention was made with support from the National Institute of Health (Grant No. R01-CA39237). Accordingly, the U.S. government may have certain rights in the invention.

FIELD OF THE INVENTION

The present invention relates generally to the manipulation of genetic materials, and, more particularly, to recombinant DNA procedures which make possible the identification of novel DNA sequences and polypeptides encoded thereby.

BACKGROUND OF THE INVENTION

Bombesin, a tetradecapeptide amide first isolated from the skin of the frog Bombina bombina, is a potent mitogen for mouse Swiss 3T3 fibroblast cells. It also stimulates secretion for guinea pig pancreatic acini. Bombesin-like peptides are produced and secreted by human small cell lung cancer cells and exogenously added bombesin-like peptides can stimulate the growth of human SCLC cells in vitro. Two examples of bombesin-like peptides are gastrin releasing peptide (GRP) and neuromedin B (NMB).

GRP is a 27 amino acid peptide amide and was first isolated from the porcine gut. The C-terminal amino acid sequence of GRP is almost identical to that of bombesin. NMB, on the other hand, is a decapeptide amide, the structure of which is almost identical to the last ten amino acids in the C-terminal region of GRP. Both GRP and NMB share high amino acid sequence homology with bombesin and indeed possess bombesin-like properties. Other bombesin-like peptides include litorin and neuromedin C (NMC).

Recent structure-function and DNA cloning studies demonstrate that at least two classes of receptors mediate the action of bombesin-like peptides. One class, the GRP preferring subtype (GRP receptor), has a high affinity for GRP and a low affinity for NMB, whereas the other class, the NMB-preferring subtype (NMB receptor), has a high affinity for NMB and lower affinity for GRP. Both classes of receptors are widely present both in the central nervous system and in the gastrointestinal tract. A third receptor class, the BRS-3 receptor, has recently been found in both rat testes and pregnant uteruses. Unlike the GRP and NMB receptors, none of the presently known bombesin-like peptide binds with high affinity ($K_d<25$ nM) to the BRS-3 receptor.

SUMMARY OF THE INVENTION

We have discovered novel genes which code for receptors capable of binding to bombesin-like peptides. The term "bombesin-like peptide" used here and below refers to a peptide capable of binding with a $K_d$ less than 1 μM to either the GRP receptor, the NMB receptor, the BRS-3 receptor, or to any other bombesin receptor subtypes such as the BB4 and BB5 receptors described below. Examples of bombesin-like peptides include, but are not limited to, bombesin, GRP, NMB, NMC, BB4 and BB5.

Accordingly, in one aspect, the invention features a pure nucleic acid (for example, genomic DNA, cDNA, or RNA) encoding a receptor for a bombesin-like peptide, the receptor including SEQ ID NO: 2, SEQ ID NO: 4, or SEQ ID NO: 6 (e.g., either as the entirety of the receptor or as a fragment thereof). In other words, a pure nucleic acid which encodes a receptor for a bobmesin-like peptide and includes SEQ ID NO: 1, SEQ ID NO: 3, or SEQ ID NO: 5; or a degenerate variant thereof embodies an aspect of this invention.

The invention also features a pure nucleic acid which (i) is capable of hybridizing to SEQ ID NO: 1, SEQ ID NO: 3, or SEQ ID NO: 5 under a high- or a low-stringency hybridization condition; and (ii) encodes a receptor protein for a bombesin-like peptide. By "low-stringency hybridization condition" is meant: prehybridization in 25% formamide, 5X SSC, 25 mM potassium phosphate buffer (pH 7.4), 5X Denhardt's, and 50 μg/ml denatured salmon sperm DNA for 4–12 hours at 37° C., which is followed by hybridization for 12–24 hours at 37° C. and washing in 2X SSC containing 0.1% SDS, at 42° C.; or an equivalent thereof. By "high-stringency hybridization condition" is meant: prehybridization in 50% formamide, 5X SSC, 25 mM potassium phosphate buffer (pH 7.4), 5X Denhardt's, and 50 μg/ml denatured salmon sperm DNA for 4–12 hours at 37° C., which is followed by hybridization for 12–24 hours at 37° C. and washing in 2X SSC containing 0.1% SDS, at 55° C.; or an equivalent thereof. E.g., see Sambrook, et al. Molecular Cloning, A Laboratory Manual, 2nd Ed. Cold Spring Harbor Laboratory Press, New York (1989), hereby incorporated by reference.

In related aspects, a cell containing one of the nucleic acids mentioned above, and a vector which includes such a nucleic acid and is capable of directing expression of the peptide encoded by that nucleic acid in a vector-containing cell are also within the scope of this invention.

Other embodiments include a pure receptor protein encoded by a nucleic acid of this invention which is capable of binding to a bombesin-like peptide, and a pure antibody which is specific for such a receptor protein.

In another aspect, this invention features a method of screening for a compound capable of interacting with a receptor protein for a bombesin-like peptide, the method comprising the steps of: (i) providing a cell which expresses a receptor protein of this invention (e.g., a native cell expressing the receptor obtained from the brain tissue, a frog egg into which mRNA encoding the receptor is introduced, or a host cells into which DNA encoding the receptor protein is introduced for expression); (ii) contacting the compound with the receptor protein expressed by the cell; and (iii) detecting an interaction, if any, between the compound and the receptor protein (e.g., binding or any biochemical response as a result of the binding).

By "pure nucleic acid" is meant a nucleic acid that is free or substantially free (i.e., at least 60% by weight free) of the DNA or RNA sequences which, in the naturally-occurring genome of the organism from which the nucleic acid of the invention is derived, flank it. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. Chemically synthesized nucleic acids are also encompassed.

By "protein" is meant any chain of amino acids, regardless of length or post-translational modification (e.g., glycosylation or phosphorylation).

By "pure receptor protein" or "pure antibody" is meant a receptor protein or antibody which has been substantially separated from components which naturally accompany it, i.e., it is at least 60%, by weight, free from the proteins and naturally-occurring organic molecules with which it is naturally associated. A pure protein (i.e., a receptor protein or an antibody of this invention) may be obtained, for example, by extraction from a natural source, by expression of a recombinant nucleic acid, or by chemical synthesis. Purity can be measured by any appropriate method, e.g., those described in column chromatography, polyacrylamide gel electrophoresis, or by HPLC analysis.

Other features and advantages of the invention will be apparent from the following description and from the claims.

BRIEF DESCRIPTION OF THE DRAWINGS

The drawings are first briefly described.

FIG. 1 is a nucleotide sequence encoding the frog BB4 receptor; the encoded amino acid sequence is also shown.

DETAILED DESCRIPTION OF THE INVENTION

Figure 2:
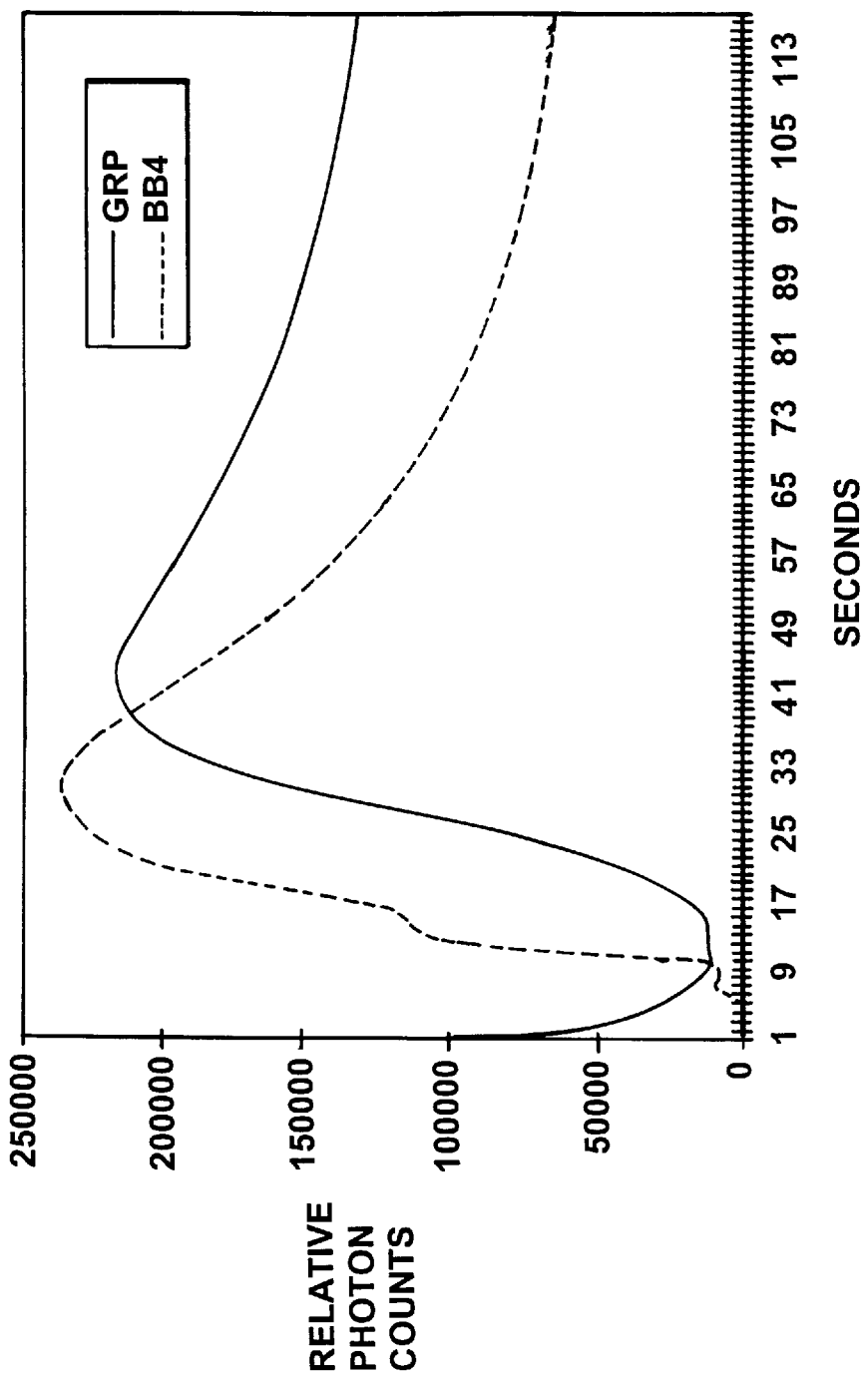
FIG. 2 is a graph showing the responses to exogenous bombesin of *Xenopus* oocytes injected respectively with RNA's encoding the human GRP receptor and the frog BB4 receptor.

Insertion of a DNA sequence of this invention into a vector, introduction of the recombinant vector thus obtained into a host cell, and subsequent expression of a receptor protein encoded by the inserted DNA sequence can be performed to produce that receptor protein. Such techniques are well known to a person of ordinary skill in the art, and in any event can be found in the literature, e.g., Sambrook, et al. Molecular Cloning, A Laboratory Manual, 2nd Ed. Cold Spring Harbor Laboratory Press, New York (1989), hereby incorporated by reference. Note that all nucleic acid sequences of this invention can be readily prepared by a person of ordinary skill in the art employing one or more the DNA sequences disclosed herein.

A receptor of this invention or its fragment (produced recombinantly, synthetically, or by conventional purification methods) can be used to generate an antibody (monoclonal or polyclonal) to be used as a diagnostic tool for detecting that receptor on cells from a given tissue, since the presence or expression level of that receptor may be related to cancer or other disorders. Of course, such an antibody can also be generated using a peptide fragment (e.g., a fragment of that receptor) which has at least one antigenic determinant that is immunologically reactive with an antigenic determinant of that receptor. Methods of generating and collecting such an antibody are well known in the art. For example, see Harlow et al., Antibodies—Laboratory Manual (1988, Cold Spring Harbor Laboratory), which is hereby incorporated by reference.

Conversely, any positively identified cells can be used to screen for compounds (e.g., a synthetic compound or the native ligand of that receptor) which interact with that receptor in various ways. As an example, bombesin-like peptides are produced and secreted by human small cell lung cancer cells (see BACKGROUND OF THE INVENTION above). Thus, some of the positively identified compounds (agonists or antagonists) can be used in the diagnosis or treatment of small cell lung cancer.

One way of detecting an interaction between a compound and the receptor of this invention is to monitor changes in intracellular calcium, as demonstrated in an actual example shown below. Alternatively, binding assays can be performed in screening for compounds which interact with the receptor. For experimental details, see von Schrenck T., et al. Am. J. Physiol. 1989; 256:G747–G758; and Moody T. W., et al., Methods Enzymol. 1989; 168:481–493, both of which are hereby incorporated by reference.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

Identification of Novel Receptors for Bombesin-Like Peptides

The rat, mouse, and human GRP receptors and the human and rat NMB receptors were aligned in a manner described in Spindel, et al., Recent Prog. Horm. Res. 1993; 48:365, 380–81, which is hereby incorporated by reference. This multiple alignment indicated certain conserved regions, based on which PCR primers and probes were prepared as tools used to look for novel receptors for bombesin-like peptides. More specifically, the following primers/probes were prepared: AT(ACT) CA(AG) CTI ACI TCI GTI GGI GTI TCI GT (SEQ ID NO: 7); (GA)TA IAG IGC (GA)AA IGG (AG)TT IAC (GA)CA IGA (GA)TT (SEQ ID NO: 8); (AC)G(ACGT) AA(AG) (AC)G(ACGT) (CT)T(ACGT) GC(ACGT) AA (SEQ ID NO: 9); and CC(ACGT) AC(GA) AA(ACGT) AC(ACGT) A(GA)(ACGT) AC (SEQ ID NO: 10). All primers/probes are written 5' to 3', mixed residues are shown in parentheses, and the symbol "I" denotes deoxyinosine.

Total RNA was then prepared by homogenization of frog brain (*Bombina orientalis*) in guanidine thiocyanate followed by centrifugation through CsCl. 5 µg total RNA was reverse transcribed with 25 pmole oligo(dT$^{18}$), 200 units of M-MLV reverse transcriptase (GIBCO-BRL, Gaithersburg, Md.), 5X buffer (250 mM Tris-HCl, pH 8.3; 375 mM KCl, 15 mM MgCl$_2$, 50 mM DTT, 2.5 mM dNTP's) in 20 µl total volume at 37° C. for 1 hour. The entire reverse transcription was used in a 100 µl PCR reaction using 100 pmoles of SEQ ID NO: 7 and 100 pmoles of SEQ ID NO: 8. PCR conditions consisted of one cycle at 92° C.×2 min, 55° C.×2 min, 72° C.×3 min for second strand synthesis, followed by 35 cycles of 92° C.×40 sec, 55° C.×1 min, 72° C.×2 min. A 20 µl-aliquot of this reaction was separated on a 1% agarose gel, transferred to a Nylon membrane and hybridized to two $^{32}$P-end labelled internal oligonucleotide probes (SEQ ID NO: 9 and SEQ ID NO: 10). The hybridizing product was subcloned into PGEM-T vector (Promega, Madison, Wis.) and sequenced as described in Nagalla, et al., J. Biol. Chem. 1992; 267:6916–22, which is hereby incorporated by reference.

Sequence analysis of multiple clones revealed a nucleotide sequence corresponding to position 585-position 1178 of SEQ ID NO: 1, which encoded amino acid sequence corresponding to position 132-position 329 of SEQ ID NO: 2. Both SEQ ID NO: 1 and 2 are shown in FIG. 1. The homology of the encoded amino acid sequence with the GRP, NMB and BRS-3 receptors was analyzed. The encoded amino acid sequence showed a 70.7% homology with the BRS-3 receptor, a 61.1% homology with the GRP receptor, and a 51.1% homology with the NMB receptor.

These results suggested that this newly discovered encoded amino acid sequence represented a new receptor subtype, which is designated as frog BB4 receptor. To prove that this receptor was not the GRP or NMB receptor, other clones were isolated from frog stomach, brain and skin mRNA that had higher (>80% homology) with their mammalian counterparts.

A cDNA library was next constructed from *B. orientalis* brain in the vector λZAP II (Stratagene, Inc., La Jolla, Calif.) using reagents and protocols provided by the supplier. To screen the cDNA library, a $^{32}$P-labeled cRNA probe was prepared from the nucleotide sequence which corresponds to position 585-position 1178 of SEQ ID NO: 1 using the T7 promoter in the PGEM-T vector. A hybridizing clone was isolated and found to encode the full coding sequence of the *Bombina orientalis* BB4 receptor. See SEQ ID NO: 1 and 2 in FIG. 1. As will be set forth below, functional studies showed that frog BB4 receptor potently responded to bombesin, suggesting that this new receptor represents the prototype receptor for the bombesin/ranatensin branch of the bombesin-like peptides and is different from the BRS-3 receptor which does not respond to bombesin.

The cDNA encoding the frog BB4 receptor was then used to screen a monkey brain cDNA library (purchased from Clontech, Inc., Palo Alto, Calif.) at low stringency (25% formamide, 5X SSC, 37° C. with washing at 50° C. in 2X SSC). Multiple hybridizing clones were isolated. Sequence analysis of the clones revealed two subtypes with partial sequences: monkey BB4 (SEQ ID NO: 3) and monkey BB5 (SEQ ID NO: 5), which encode SEQ ID NO: 4 and SEQ ID NO: 6, respectively. Monkey BB4 appears highly homologous to frog BB4, i.e., an 88.1% homology in the 84 amino acid overlap. SEQ ID NO: 3, 4, 5 and 6 are shown below:

SEQ ID NO: 3
CAGACATCTG ACGCGGTGTT GAAGACGTGC GGCAAAGCTG TTTGTGTTTG
GATTATCTCC ATGCTACTTG CTGCCCCTGA GGCAGTGTTT TCGGATTTGT
ATGAATTCAC CAGCCCTGAC AAGAATATGT CCTTCAAAAC ATGTGCCCCT
TATCCTGTTT CTGAAAAGCT ACTGCAAGAG ACACATTCGC TGATGTGCTT
CTTAGTGTTC TATATTATTC CCTTGTCTAT TATCTCCGCC TACTACTTCC TC

SEQ ID NO: 4
Gln Thr Ser Asp Ala Val Leu Lys Thr Cys Gly Lys Ala Val Cys
Val Trp Ile Ile Ser Met Leu Leu Ala Ala Pro Glu Ala Val Phe
Ser Asp Leu Tyr Glu Phe Thr Ser Pro Asp Lys Asn Met Ser Phe
Lys Thr Cys Ala Pro Tyr Pro Val Ser Glu Lys Leu Leu Gln Glu
Thr His Ser Leu Met Cys Phe Leu Val Phe Tyr Ile Ile Pro Leu
Ser Ile Ile Ser Ala Tyr Tyr Phe Leu

SEQ ID NO: 5
CAGACCTCAG ATGCTGTGCT GAAGACCTGT GCCAAAGCTG GTGGCATCTG
GATCATGGCT ATGATATTTG CTCTGCCAGA GGCTATATTC TCAAATGTAT
ACACTTTCCA AGGTCCTAAC AGAAACGTAA CATTTGAATC CTGTAACTCC
TACCCTATCT CTGAGAGGCT TTTGCAGGAA ATACATTCTC TGTTGTGTTT
CTTGGTGTTC TACATTATCC CGCTCTCGAT TATCTCCGCC TATTACTTCC

SEQ ID NO: 6
Gln Thr Ser Asp Ala Val Leu Lys Thr Cys Ala Lys Ala Gly Gly
Ile Trp Ile Met Ala Met Ile Phe Ala Leu Pro Glu Ala Ile Phe
Ser Asn Val Tyr Thr Phe Gln Gly Pro Asn Arg Asn Val Thr Phe
Glu Ser Cys Asn Ser Tyr Pro Ile Ser Glu Arg Leu Leu Gln Glu
Ile His Ser Leu Leu Cys Phe Leu Val Phe Tyr Ile Ile Pro Leu
Ser Ile Ile Ser Ala Tyr Tyr Phe

Function Studies (Changes in Intracellular Calcium)

To prepare the receptor RNA for injection into Xenopus oocytes, the linearized cDNA encoding frog BB4 receptor, was phenol extracted, ethanol precipitated, and then transcribed with T7 or T3 RNA polymerase. Transcription reactions were carried out in a 50–100 μl volume containing 5–20 μg DNA template, 40 mM Tris (pH 7.9), 7 mM $MgCl_2$, 10 mM DTT, 2 mM spermidine, 10 mM NaCl, 25 μg/ml BSA, 0.5 mM ATP, 0.5 mM UTP, 0.5 mM CTP, 0.2 mM GTP, 1 mM 7-Me GpppG (Pharmacia, Piscataway, N.J.), 50–100 units RNA polymerase and 125–250 units RNasin (Promega, Madison, Wis.). The reactions were incubated at 40° C. for 90 minutes, treated with FPLC purified DNase (Pharmacia, Piscataway, N.J.), phenol extracted twice, ethanol precipitated twice, and then resuspended in 5–10 μl $H_2O$. See Julius, et al. Science 1988; 241:558–564, which is hereby incorporated by reference.

To measure bombesin-induced changes in intracellular calcium, the procedure described in Sandberg, et al. FEBS Lett 1988; 241:177–180 (hereby incorporated by reference) was followed with some modifications (see Spindel, et al., Mol. Endocrinol. 1990; 4:1956–1963; and Giladi, et al., Biotechniques 1991; 10:744–747) to determine, both of which are hereby incorproated by reference). More specifically, oocytes were removed from an albino Xenopus, treated with collagenase, defollicated, and then injected in the presence of OR-2 (a buffer solution suitable for frog oocytes) without calcium. The injection needles were rinsed with 1 mM EDTA before each use. For injection, the transcribed RNA (typically, 1–2 μl) was dried down and then suspended in an equal volume of an aequorin solution. The aequorin solution was prepared at a concentration of 1 mg/ml in 1 mM EDTA and stored in aliquots at −85° C.. Aequorin was obtained from Friday Harbor Photoproteins, Friday Harbor, Wash.

To record the bombesin-induced response, oocytes were placed in 500 μl OR-2 in 12×55 mm disposable polystyrene tubes in a luminometer. Light output from the oocyte as recorded by the luminometer is a function of ligand-induced increases in intracellular calcium. The baseline response to OR-2 was first recorded, followed by the recording of the response to bombesin.

As a positive control, *Xenopus* oocytes containing exogenous human GRP receptor were also prepared and assayed in analogous manners.

FIG. 2 demonstrates the respective responses of GRP and BB4 receptors to 1 nM (in the OR-2 buffer) of bombesin. It is clear that the BB4 receptor, unlike the BRS-3 receptor, potently responded to bombesin.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, contemplated equivalents of this invention include nucleic acid or peptide sequences which are substantially identical to those clearly described above and explicitly claimed below. By "substantially identical" is meant a nucleic acid or peptide exhibiting at least 50%, preferably 85%, more preferably 90%, and most preferably 95% homology to a reference amino acid or nucleic acid sequence. For peptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: (i) glycine, alanine; (ii) valine, isoleucine, leucine; (iii) aspartic acid, glutamic acid, asparagine, glutamine; (iv) serine, threonine; (v) lysine, arginine; and (vi) phenylalanine, tyrosine.

Furthermore, nucleic acide and peptides which are allelic variations, natural mutants, and induced mutants are also within the scope of this invention.

Still other contemplated equivalents of this invention include peptides which are shorter than a receptor of this invention (e.g., a fragment thereof) which has at least one antigenic determinant that is immunologically reactive with an antigenic determinant of that receptor.

Other embodiments are also within the claims set forth below.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1563 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 192...1319

( x i ) SEQUENCE DESCRIPTION: SEQ ID NO:1:

```
CACGAGTGCA  AGCACTAAAC  CACCCTAGTG  CTGATGAGAG  CTGTGATTTC  TGGAGATACC            60

GAGTTTGTGG  ACATCAATTA  GGTTTCATTT  GTGGAACTTT  AATTGAGGTC  ACTTGTGTGC           120

TGCAATTCAT  GAACTTGAAA  CTGCTGAAGA  AGAAATTTGG  AACAACTGAA  TTTTATTTAG           180

ATTAAAAAAA  A ATG CCT GAA GGT TTT CAG TCA CTT AAC CAG ACA TTG CCA               230
              Met Pro Glu Gly Phe Gln Ser Leu Asn Gln Thr Leu Pro
                1               5                      10

TCT GCT ATA AGT AGC ATA GCT CAT TTG GAA TCC CTT AAT GAC AGT TTC                 278
Ser Ala Ile Ser Ser Ile Ala His Leu Glu Ser Leu Asn Asp Ser Phe
        15              20                      25

ATT TTA GGT GCA AAG CAA AGT GAA GAT GTA TCC CCT GGG TTA GAA ATA                 326
Ile Leu Gly Ala Lys Gln Ser Glu Asp Val Ser Pro Gly Leu Glu Ile
 30              35                      40                      45

CTG GCT CTA ATT TCT GTC ACA TAT GCT GTT ATT ATT TCT GTC GGT ATC                 374
Leu Ala Leu Ile Ser Val Thr Tyr Ala Val Ile Ile Ser Val Gly Ile
                 50                      55                      60

CTT GGA AAC ACA ATA CTT ATA AAA GTA TTT TTT AAA ATC AAG TCA ATG                 422
Leu Gly Asn Thr Ile Leu Ile Lys Val Phe Phe Lys Ile Lys Ser Met
             65              70                      75

CAG ACT GTT CCT AAT ATT TTC ATC ACC AGC CTG GCT TTT GGA GAT CTT                 470
Gln Thr Val Pro Asn Ile Phe Ile Thr Ser Leu Ala Phe Gly Asp Leu
         80                      85                      90

CTT CTA CTG CTG ACC TGC GTG CCA GTG GAC GCA TCT CGG TAT ATT GTG                 518
Leu Leu Leu Leu Thr Cys Val Pro Val Asp Ala Ser Arg Tyr Ile Val
     95                     100                     105

GAC ACG TGG ATG TTT GGA AGA GCT GGC TGT AAG ATA ATT TCC TTC ATA                 566
Asp Thr Trp Met Phe Gly Arg Ala Gly Cys Lys Ile Ile Ser Phe Ile
```

```
         110                       115                        120                          125
CAG  CTT  ACC  TCT  GTC  GGA  GTG  TCG  GTG  TTT  ACT  TTA  ACT  GTC  CTC  AGT        614
Gln  Leu  Thr  Ser  Val  Gly  Val  Ser  Val  Phe  Thr  Leu  Thr  Val  Leu  Ser
                    130                      135                          140

ACT  GAC  AGG  TAC  AGA  GCC  ATT  GTG  AAA  CCC  TTG  CAA  TTG  CAG  ACC  TCA        662
Thr  Asp  Arg  Tyr  Arg  Ala  Ile  Val  Lys  Pro  Leu  Gln  Leu  Gln  Thr  Ser
               145                           150                    155

GAT  GCC  GTT  TTG  AAG  ACA  TGT  GGC  AAA  GCT  GTT  TGT  GTT  TGG  ATC  ATT        710
Asp  Ala  Val  Leu  Lys  Thr  Cys  Gly  Lys  Ala  Val  Cys  Val  Trp  Ile  Ile
          160                          165                     170

TCC  ATG  CTC  CTC  GCT  GCT  CCA  GAA  GCT  GTG  TTC  TCA  GAT  TTG  TAT  GAA        758
Ser  Met  Leu  Leu  Ala  Ala  Pro  Glu  Ala  Val  Phe  Ser  Asp  Leu  Tyr  Glu
     175                           180                     185

TTT  GGC  AGC  TCG  GAA  AAA  AAT  ACC  ACT  TTT  GAA  GCC  TGT  GCT  CCA  TAT        806
Phe  Gly  Ser  Ser  Glu  Lys  Asn  Thr  Thr  Phe  Glu  Ala  Cys  Ala  Pro  Tyr
190                      195                      200                          205

CCA  GTC  TCT  GAA  AAG  ATT  CTG  CAA  GAG  ACA  CAT  TCC  CTA  ATA  TGC  TTC        854
Pro  Val  Ser  Glu  Lys  Ile  Leu  Gln  Glu  Thr  His  Ser  Leu  Ile  Cys  Phe
                    210                      215                          220

CTG  GTA  TTC  TAC  ATT  GTT  CCC  CTG  TCA  ATC  ATT  TCT  GCA  TAT  TAC  TTC        902
Leu  Val  Phe  Tyr  Ile  Val  Pro  Leu  Ser  Ile  Ile  Ser  Ala  Tyr  Tyr  Phe
               225                           230                    235

CTT  ATT  GCA  AAA  ACC  CTG  TAC  AAA  AGT  ACT  TTC  AAC  ATG  CCT  GCT  GAA        950
Leu  Ile  Ala  Lys  Thr  Leu  Tyr  Lys  Ser  Thr  Phe  Asn  Met  Pro  Ala  Glu
          240                          245                     250

GAG  CAC  ACT  CAC  GCC  CGA  AAA  CAG  ATA  GAA  TCG  CGC  AAA  CGA  GTG  GCA        998
Glu  His  Thr  His  Ala  Arg  Lys  Gln  Ile  Glu  Ser  Arg  Lys  Arg  Val  Ala
     255                           260                     265

AAA  ACT  GTG  TTG  GTG  TTG  GTG  GCA  TTG  TTC  GCA  GTG  TGC  TGG  TTG  CCA       1046
Lys  Thr  Val  Leu  Val  Leu  Val  Ala  Leu  Phe  Ala  Val  Cys  Trp  Leu  Pro
270                      275                      280                          285

AAC  CAC  ATG  CTC  TAC  TTG  TAT  CGA  TCC  TTC  ACA  TAT  CAC  TCC  GCA  GTG       1094
Asn  His  Met  Leu  Tyr  Leu  Tyr  Arg  Ser  Phe  Thr  Tyr  His  Ser  Ala  Val
                    290                      295                          300

AAT  TCC  TCT  GCG  TTT  CAC  CTG  TCA  GCC  ACA  ATC  TTT  GCG  CGA  GTA  CTG       1142
Asn  Ser  Ser  Ala  Phe  His  Leu  Ser  Ala  Thr  Ile  Phe  Ala  Arg  Val  Leu
               305                           310                    315

GCT  TTG  CGC  AAT  TCC  TGC  GTC  AAC  CCC  TTC  GCC  CTC  TAT  TGG  CTA  AGC       1190
Ala  Leu  Arg  Asn  Ser  Cys  Val  Asn  Pro  Phe  Ala  Leu  Tyr  Trp  Leu  Ser
          320                          325                     330

AAG  AGC  TTT  AGG  CAG  CAT  TTT  AAA  AAG  CAA  GTG  TAT  TGT  TGT  AAG  ACT       1238
Lys  Ser  Phe  Arg  Gln  His  Phe  Lys  Lys  Gln  Val  Tyr  Cys  Cys  Lys  Thr
     335                           340                     345

GAA  CCT  CTG  CAT  CCA  ACA  AAG  TCC  GAC  CCA  CAG  CAG  TAC  CAT  AAC  TGG       1286
Glu  Pro  Leu  His  Pro  Thr  Lys  Ser  Asp  Pro  Gln  Gln  Tyr  His  Asn  Trp
350                      355                      360                          365

AAT  TAC  CGC  TGT  GAA  AGG  CAA  CAT  CCA  GAT  GTC  TGAAATTAGC ATTACATTAT         1339
Asn  Tyr  Arg  Cys  Glu  Arg  Gln  His  Pro  Asp  Val
                    370                      375

TAAGTGCTTA CGATGTAAAG AAAGAGTGAC AGTGTCGCCA AATAAGTTAT AAAAAGTTTA                   1399

TAAAACTTAC TGTAAACAAA AGATGGATAA AGTTTTGTT GCTGCATATT GACGTCTGTT                   1459

TATTAAAAAT CCAGAGTATA AAGTTTTATT ACTACAAACA AAAAAATATA CCTCAACATT                   1519

CTAACCACAA TTGAATTATT CATATATTAC CCTTATTTAT TCAG                                    1563
```

( 2 ) INFORMATION FOR SEQ ID NO:2:

( i ) SEQUENCE CHARACTERISTICS:
        ( A ) LENGTH: 376 amino acids
        ( B ) TYPE: amino acid (D) TOPOLOGY: Not Relevant (xi) SEQUENCE DESCRIPTION: SEQ ID NO:2:

| | | | | | | | | | | | | | | |
|---|---|---|---|---|---|---|---|---|---|---|---|---|---|---|
| Met<br>1 | Pro | Glu | Gly | Phe<br>5 | Gln | Ser | Leu | Asn | Thr<br>10 | Leu | Pro | Ser | Ala | Ile<br>15 |
| Ser | Ser | Ile | Ala<br>20 | His | Leu | Glu | Ser | Leu<br>25 | Asn | Asp | Ser | Phe | Ile<br>30 | Leu | Gly |
| Ala | Lys | Gln<br>35 | Ser | Glu | Asp | Val | Ser<br>40 | Pro | Gly | Leu | Glu | Ile<br>45 | Leu | Ala | Leu |
| Ile | Ser<br>50 | Val | Thr | Tyr | Ala | Val<br>55 | Ile | Ile | Ser | Val | Gly<br>60 | Ile | Leu | Gly | Asn |
| Thr<br>65 | Ile | Leu | Ile | Lys | Val<br>70 | Phe | Phe | Lys | Ile | Lys<br>75 | Ser | Met | Gln | Thr | Val<br>80 |
| Pro | Asn | Ile | Phe | Ile<br>85 | Thr | Ser | Leu | Ala | Phe<br>90 | Gly | Asp | Leu | Leu | Leu<br>95 | Leu |
| Leu | Thr | Cys | Val<br>100 | Pro | Val | Asp | Ala | Ser<br>105 | Arg | Tyr | Ile | Val | Asp<br>110 | Thr | Trp |
| Met | Phe | Gly<br>115 | Arg | Ala | Gly | Cys | Lys<br>120 | Ile | Ile | Ser | Phe | Ile<br>125 | Gln | Leu | Thr |
| Ser | Val<br>130 | Gly | Val | Ser | Val | Phe<br>135 | Thr | Leu | Thr | Val | Leu<br>140 | Ser | Thr | Asp | Arg |
| Tyr<br>145 | Arg | Ala | Ile | Val | Lys<br>150 | Pro | Leu | Gln | Leu | Gln<br>155 | Thr | Ser | Asp | Ala | Val<br>160 |
| Leu | Lys | Thr | Cys | Gly<br>165 | Lys | Ala | Val | Cys | Val<br>170 | Trp | Ile | Ile | Ser | Met<br>175 | Leu |
| Leu | Ala | Ala | Pro<br>180 | Glu | Ala | Val | Phe | Ser<br>185 | Asp | Leu | Tyr | Glu | Phe<br>190 | Gly | Ser |
| Ser | Glu | Lys<br>195 | Asn | Thr | Thr | Phe | Glu<br>200 | Ala | Cys | Ala | Pro | Tyr<br>205 | Pro | Val | Ser |
| Glu | Lys<br>210 | Ile | Leu | Gln | Glu | Thr<br>215 | His | Ser | Leu | Ile | Cys<br>220 | Phe | Leu | Val | Phe |
| Tyr<br>225 | Ile | Val | Pro | Leu | Ser<br>230 | Ile | Ile | Ser | Ala | Tyr<br>235 | Tyr | Phe | Leu | Ile | Ala<br>240 |
| Lys | Thr | Leu | Tyr | Lys<br>245 | Ser | Thr | Phe | Asn | Met<br>250 | Pro | Ala | Glu | Glu | His<br>255 | Thr |
| His | Ala | Arg | Lys<br>260 | Gln | Ile | Glu | Ser | Arg<br>265 | Lys | Arg | Val | Ala | Lys<br>270 | Thr | Val |
| Leu | Val | Leu<br>275 | Val | Ala | Leu | Phe | Ala<br>280 | Val | Cys | Trp | Leu | Pro<br>285 | Asn | His | Met |
| Leu | Tyr<br>290 | Leu | Tyr | Arg | Ser | Phe<br>295 | Thr | Tyr | His | Ser | Ala<br>300 | Val | Asn | Ser | Ser |
| Ala<br>305 | Phe | His | Leu | Ser | Ala<br>310 | Thr | Ile | Phe | Ala | Arg<br>315 | Val | Leu | Ala | Leu | Arg<br>320 |
| Asn | Ser | Cys | Val | Asn<br>325 | Pro | Phe | Ala | Leu | Tyr<br>330 | Trp | Leu | Ser | Lys | Ser<br>335 | Phe |
| Arg | Gln | His<br>340 | Phe | Lys | Lys | Gln | Val<br>345 | Tyr | Cys | Cys | Lys | Thr<br>350 | Glu | Pro | Leu |
| His | Pro | Thr<br>355 | Lys | Ser | Asp | Pro | Gln<br>360 | Gln | Tyr | His | Asn | Trp<br>365 | Asn | Tyr | Arg |
| Cys | Glu<br>370 | Arg | Gln | His | Pro | Asp<br>375 | Val | | | | | | | | |

(2) INFORMATION FOR SEQ ID NO:3:

(i) SEQUENCE CHARACTERISTICS:

(A) LENGTH: 252 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 1...252

(xi) SEQUENCE DESCRIPTION: SEQ ID NO:3:

| CAG | ACA | TCT | GAC | GCG | GTG | TTG | AAG | ACG | TGC | GGC | AAA | GCT | GTT | TGT | GTT | 48 |
|---|---|---|---|---|---|---|---|---|---|---|---|---|---|---|---|---|
| Gln | Thr | Ser | Asp | Ala | Val | Leu | Lys | Thr | Cys | Gly | Lys | Ala | Val | Cys | Val | |
| 1 | | | | 5 | | | | | 10 | | | | | 15 | | |

| TGG | ATT | ATC | TCC | ATG | CTA | CTT | GCT | GCC | CCT | GAG | GCA | GTG | TTT | TCG | GAT | 96 |
|---|---|---|---|---|---|---|---|---|---|---|---|---|---|---|---|---|
| Trp | Ile | Ile | Ser | Met | Leu | Leu | Ala | Ala | Pro | Glu | Ala | Val | Phe | Ser | Asp | |
| | | | 20 | | | | | 25 | | | | | 30 | | | |

| TTG | TAT | GAA | TTC | ACC | AGC | CCT | GAC | AAG | AAT | ATG | TCC | TTC | AAA | ACA | TGT | 144 |
|---|---|---|---|---|---|---|---|---|---|---|---|---|---|---|---|---|
| Leu | Tyr | Glu | Phe | Thr | Ser | Pro | Asp | Lys | Asn | Met | Ser | Phe | Lys | Thr | Cys | |
| | | 35 | | | | | 40 | | | | | 45 | | | | |

| GCC | CCT | TAT | CCT | GTT | TCT | GAA | AAG | CTA | CTG | CAA | GAG | ACA | CAT | TCG | CTG | 192 |
|---|---|---|---|---|---|---|---|---|---|---|---|---|---|---|---|---|
| Ala | Pro | Tyr | Pro | Val | Ser | Glu | Lys | Leu | Leu | Gln | Glu | Thr | His | Ser | Leu | |
| | 50 | | | | | 55 | | | | | 60 | | | | | |

| ATG | TGC | TTC | TTA | GTG | TTC | TAT | ATT | ATT | CCC | TTG | TCT | ATT | ATC | TCC | GCC | 240 |
|---|---|---|---|---|---|---|---|---|---|---|---|---|---|---|---|---|
| Met | Cys | Phe | Leu | Val | Phe | Tyr | Ile | Ile | Pro | Leu | Ser | Ile | Ile | Ser | Ala | |
| 65 | | | | | 70 | | | | | 75 | | | | | 80 | |

| TAC | TAC | TTC | CTC | 252 |
|---|---|---|---|---|
| Tyr | Tyr | Phe | Leu | |

(2) INFORMATION FOR SEQ ID NO:4:

(i) SEQUENCE CHARACTERISTICS:
(A) LENGTH: 84 amino acids
(B) TYPE: amino acid
(D) TOPOLOGY: Not Relevant (xi) SEQUENCE DESCRIPTION: SEQ ID NO:4:

| Gln | Thr | Ser | Asp | Ala | Val | Leu | Lys | Thr | Cys | Gly | Lys | Ala | Val | Cys | Val |
|---|---|---|---|---|---|---|---|---|---|---|---|---|---|---|---|
| 1 | | | | 5 | | | | | 10 | | | | | 15 | |

| Trp | Ile | Ile | Ser | Met | Leu | Leu | Ala | Ala | Pro | Glu | Ala | Val | Phe | Ser | Asp |
|---|---|---|---|---|---|---|---|---|---|---|---|---|---|---|---|
| | | | 20 | | | | | 25 | | | | | 30 | | |

| Leu | Tyr | Glu | Phe | Thr | Ser | Pro | Asp | Lys | Asn | Met | Ser | Phe | Lys | Thr | Cys |
|---|---|---|---|---|---|---|---|---|---|---|---|---|---|---|---|
| | | 35 | | | | | 40 | | | | | 45 | | | |

| Ala | Pro | Tyr | Pro | Val | Ser | Glu | Lys | Leu | Leu | Gln | Glu | Thr | His | Ser | Leu |
|---|---|---|---|---|---|---|---|---|---|---|---|---|---|---|---|
| | 50 | | | | | 55 | | | | | 60 | | | | |

| Met | Cys | Phe | Leu | Val | Phe | Tyr | Ile | Ile | Pro | Leu | Ser | Ile | Ile | Ser | Ala |
|---|---|---|---|---|---|---|---|---|---|---|---|---|---|---|---|
| 65 | | | | | 70 | | | | | 75 | | | | | 80 |

| Tyr | Tyr | Phe | Leu |
|---|---|---|---|

(2) INFORMATION FOR SEQ ID NO:5:

(i) SEQUENCE CHARACTERISTICS:
(A) LENGTH: 250 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 1...249

(xi) SEQUENCE DESCRIPTION: SEQ ID NO:5:

| CAG | ACC | TCA | GAT | GCT | GTG | CTG | AAG | ACC | TGT | GCC | AAA | GCT | GGT | GGC | ATC | 48 |
|---|---|---|---|---|---|---|---|---|---|---|---|---|---|---|---|---|
| Gln | Thr | Ser | Asp | Ala | Val | Leu | Lys | Thr | Cys | Ala | Lys | Ala | Gly | Gly | Ile | |
| 1 | | | | 5 | | | | | 10 | | | | | 15 | | |

-continued

| TGG | ATC | ATG | GCT | ATG | ATA | TTT | GCT | CTG | CCA | GAG | GCT | ATA | TTC | TCA | AAT | 96 |
| Trp | Ile | Met | Ala | Met | Ile | Phe | Ala | Leu | Pro | Glu | Ala | Ile | Phe | Ser | Asn | |
| | | | 20 | | | | | 25 | | | | | 30 | | | |

| GTA | TAC | ACT | TTC | CAA | GGT | CCT | AAC | AGA | AAC | GTA | ACA | TTT | GAA | TCC | TGT | 144 |
| Val | Tyr | Thr | Phe | Gln | Gly | Pro | Asn | Arg | Asn | Val | Thr | Phe | Glu | Ser | Cys | |
| | | 35 | | | | | | 40 | | | | | 45 | | | |

| AAC | TCC | TAC | CCT | ATC | TCT | GAG | AGG | CTT | TTG | CAG | GAA | ATA | CAT | TCT | CTG | 192 |
| Asn | Ser | Tyr | Pro | Ile | Ser | Glu | Arg | Leu | Leu | Gln | Glu | Ile | His | Ser | Leu | |
| | 50 | | | | | 55 | | | | | 60 | | | | | |

| TTG | TGT | TTC | TTG | GTG | TTC | TAC | ATT | ATC | CCG | CTC | TCG | ATT | ATC | TCC | GCC | 240 |
| Leu | Cys | Phe | Leu | Val | Phe | Tyr | Ile | Ile | Pro | Leu | Ser | Ile | Ile | Ser | Ala | |
| 65 | | | | | 70 | | | | | 75 | | | | | 80 | |

| TAT | TAC | TTC | C | | | | | | | | | | | | | 250 |
| Tyr | Tyr | Phe | | | | | | | | | | | | | | |

( 2 ) INFORMATION FOR SEQ ID NO:6:

( i ) SEQUENCE CHARACTERISTICS:
        ( A ) LENGTH: 83 amino acids
        ( B ) TYPE: amino acid
        ( D ) TOPOLOGY: Not Relevant ( x i ) SEQUENCE DESCRIPTION: SEQ ID NO:6:

| Gln | Thr | Ser | Asp | Ala | Val | Leu | Lys | Thr | Cys | Ala | Lys | Ala | Gly | Gly | Ile |
| 1 | | | | 5 | | | | | 10 | | | | | 15 | |

| Trp | Ile | Met | Ala | Met | Ile | Phe | Ala | Leu | Pro | Glu | Ala | Ile | Phe | Ser | Asn |
| | | | 20 | | | | | 25 | | | | | 30 | | |

| Val | Tyr | Thr | Phe | Gln | Gly | Pro | Asn | Arg | Asn | Val | Thr | Phe | Glu | Ser | Cys |
| | | 35 | | | | | | 40 | | | | | 45 | | |

| Asn | Ser | Tyr | Pro | Ile | Ser | Glu | Arg | Leu | Leu | Gln | Glu | Ile | His | Ser | Leu |
| | 50 | | | | | 55 | | | | | 60 | | | | |

| Leu | Cys | Phe | Leu | Val | Phe | Tyr | Ile | Ile | Pro | Leu | Ser | Ile | Ile | Ser | Ala |
| 65 | | | | | 70 | | | | | 75 | | | | | 80 |

| Tyr | Tyr | Phe |

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( B ) LOCATION: 9, 12, 15, 18, 21, 24 and 27
        ( D ) OTHER INFORMATION: where N at each of positions 9, 12,
            15, 18, 21, 24 and 27 is deoxyinosine ( x i ) SEQUENCE DESCRIPTION: SEQ ID NO:7:

ATHCARCTNA CNTCNGTNGG NGTNTCNGT                              29

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( B ) LOCATION: 4, 7, 13, 19 and 25
        ( D ) OTHER INFORMATION: where N at each of positions 4, 7, 13,
            19 and 25 is deoxyinosine ( x i ) SEQUENCE DESCRIPTION: SEQ ID NO:8:

-continued

```
RTANAGNGCR  AANGGRTTNA  CRCANGARTT                                    30
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (B) LOCATION: 3, 9, 12 and 15
        (D) OTHER INFORMATION: where N at each of positions 3, 9, 12 and 15 is A, C, G or T (xi) SEQUENCE DESCRIPTION: SEQ ID NO:9:

```
MGNAARMGNY  TNGCNAA                                                   17
```

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (B) LOCATION: 3, 9, 12 and 15
        (D) OTHER INFORMATION: where N at each of positions 3, 9, 12 and 15 is A, C, G or T (xi) SEQUENCE DESCRIPTION: SEQ ID NO:10:

```
CCNACRAANA  CNARNAC                                                   17
```

What is claimed is:

1. A method of screening for a compound which interacts with a receptor protein for a bombesin-like peptide, said method comprising:

providing a host cell transfected with the nucleic acid encoding a receptor protein for a bombesin-like peptide, comprising the amino acid sequence as set forth in SEQ ID NO: 2;

culturing the host cell under conditions that would allow expression of the receptor protein on the surface of the host cell;

contacting the compound with the receptor protein; and detecting an interaction between the compound and said expressed receptor protein.

\* \* \* \* \*